(12) United States Patent
He et al.

(10) Patent No.: US 6,384,105 B1
(45) Date of Patent: *May 7, 2002

(54) POLY(PROPYLENE FUMARATE) CROSS LINKED WITH POLY(ETHYLENE GLYCOL)

(75) Inventors: Shulin He, Houston, TX (US); Michael J. Yaszemski, Rochester, MN (US); Antonios G. Mikos, Houston, TX (US)

(73) Assignee: William Marsh Rice University, Houston, TX (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/550,372

(22) Filed: Apr. 14, 2000

Related U.S. Application Data

(60) Provisional application No. 60/129,577, filed on Apr. 16, 1999, provisional application No. 60/146,991, filed on Aug. 3, 1999, provisional application No. 60/167,328, filed on Nov. 24, 1999, and provisional application No. 60/167,388, filed on Nov. 24, 1999.

(51) Int. Cl.[7] .............................. C08F 8/28; A61F 2/28
(52) U.S. Cl. ....................... 523/113; 523/115; 525/385; 525/386
(58) Field of Search ................................ 528/447, 301, 528/306; 523/113, 115, 523; 525/385, 386

(56) References Cited

U.S. PATENT DOCUMENTS

| | | | | |
|---|---|---|---|---|
| 3,701,748 A | * | 10/1972 | Kroekel | 525/386 |
| 4,843,112 A | | 6/1989 | Gerhart et al. | 523/114 |
| 4,888,413 A | * | 12/1989 | Domb | 528/272 |
| 5,286,763 A | * | 2/1994 | Gerhart et al. | 514/772.4 |
| 5,364,627 A | * | 11/1994 | Song | 424/443 |
| 5,420,179 A | * | 5/1995 | Fourquier et al. | 523/523 |
| 5,733,951 A | * | 3/1998 | Yaszemski et al. | 523/116 |
| 5,989,579 A | * | 11/1999 | Daronger et al. | 427/427 |
| 6,071,982 A | * | 6/2000 | Wise et al. | 523/113 |
| 6,124,373 A | * | 9/2000 | Peter et al. | 523/116 |
| 6,153,664 A | * | 11/2000 | Wise et al. | 523/115 |

* cited by examiner

Primary Examiner—Veronica P. Hoke
(74) Attorney, Agent, or Firm—Conley, Rose & Tayon, P.C.

(57) ABSTRACT

New injectable, in situ crosslinkable biodegradable polymer composites comprise poly(propylene fumarate) (PPF), poly (ethylene glycol)-dimethacrylate (PEG-DMA), an, optionally, β-tricalcium phosphate (β-TCP). A method for controlling the crosslinking characteristics of the composites, including the maximum crosslinking temperature and the gel point, as well as the properties of the cross linked composites such as the compressive strength and modulus and the water holding capacity, is disclosed.

12 Claims, 2 Drawing Sheets

POLY(PROPYLENE FUMARATE) CROSS LINKED WITH POLY(ETHYLENE GLYCOL)

RELATED CASES

The present case claims the benefit of U.S. provisional applications Ser. No. 60/129,577, filed Apr. 16, 1999, and entitled "Development of Biodegradable Bone Cement Based on Poly(Propylene Fumarate) and a Macromer," Ser. No. 60/146,991, filed Aug. 3, 1999, and entitled "Synthesis of Poly(Propylene Fumarate) by Acylation of Propylene Glycol in the Presence of a Proton Scavenger," Ser. No. 60/167,328, filed Nov. 24, 1999, and entitled "Preparation of an Injectable, in situ Polymerizable and Biodegradable Biomaterial Based On Poly(Propylene Fumarate) and Biodegradable Cross linking Reagents," and Ser. No. 60/167,388, filed Nov. 24, 1999, and entitled "Injectable Biodegradable Polymer Composites Based on Poly(Propylene Fumarate) Cross linked with Poly(Ethylene Glycol)-Dimethacrylate and β-Tricalcium Phosphate," all of which are incorporated herein by reference.

STATEMENT REGARDING FEDERALLY SPONSORED RESEARCH OR DEVELOPMENT

This work was funded by the National Institutes of Health R01-AR44381 and R01-DE13031.

TECHNICAL FIELD OF THE INVENTION

This invention relates to a compound for replacing or reconstructing rigid or semi-rigid living tissue. More particularly, the present invention relates to compositions comprising poly(propylene fumarate) cross linked with poly(ethylene glycol) and methods for making these compositions.

BACKGROUND OF THE INVENTION

In the field of tissue engineering, degradable biomaterials usually serve as a scaffold to provide mechanical support and a matrix for the ingrowth of new tissue. As new tissue forms on the scaffold, the biomaterial degrades until it is entirely dissolved. The degradation products are eliminated through the body's natural pathways, such as metabolic processes.

One example of the use of such biomaterials is as a temporary bone replacement. It is often desired to replace or reconstruct all or a portion of a living bone, such as when a bone has been broken or has been resected as a result of a bone tumor. In these instances, the missing bone can be replaced with a mechanical device, such as a pin, plate or the like, or it can be replaced with an implant that is designed to more closely resemble the original bone itself. Often these implants comprise biodegradable polymeric compounds or parts made from such compounds. It is contemplated that bone tissue will grow back into the pores of the implant and will gradually replace the entire implant as the implant itself is gradually degraded in the in vivo environment. For obvious reasons then, such implants should be biocompatible and non-toxic.

Poly(propylene fumarate) (PPF) is one such polymer. Poly(propylene fumarate) (hereinafter "PPF") is an unsaturated linear polyester that degrades in the presence of water into propylene glycol and fulmaric acid, degradation products that are easily cleared from the human body by normal metabolic processes. Because the fumarate double bonds in PPF are reactive and cross link at low temperatures, PPF has potential to be an effective in situ polymerizable biomaterial.

The high mechanical strength of cured PPF matrices and their ability to be cross linked in situ makes them especially suitable for orthopedic application. Another advantage of cured PPF matrices is that they biodegrade into non-toxic propylene glycol and fumaric acid. On the basis of these unique properties, PPF has been formulated as bone cement, an orthopaedic scaffold for bone tissue regeneration, and a drug delivery system.

Several PPF-based formulation methods have been evaluated by varying such parameters as the molecular weight of PPF and the choice of cross linking reagents. For example, U.S. Pat. No. 5,733,951 discloses a composite mixture incorporating P(PF), a cross linking monomer (N-vinyl pyrrolidone), a porogen (sodium chloride), and a particulate phase (β-tricalcium phosphate) that can be injected or inserted into skeletal defects of irregular shape or size.

The properties of some PPF composites can be tailored for specific applications by varying different parameters, including crosslinking density and molecular weight of PPF. PPF composite formulations can include a porogen such as NaCl for initial porosity and a particulate ceramic such as β-TCP for mechanical reinforcement and increased osteoconductivity. PPF composite formulations can also include a vinyl monomer such as N-vinyl pyrrolidone, which serves as a crosslinking reagent. However, because this monomer is toxic, any unreacted amount during polymerization in situ may present a problem.

Poly(ethylene glycol), (PEG), is a hydrophilic polyether that has received much attention for use in biomaterials because low molecular weight PEG is passively excreted by the body. PEG has also been covalently bound to polyesters in an effort to increase polyester biocompatibility. The use of acrylated PEG as a nontoxic crosslinking reagent to produce polymer networks with acrylated poly(lactic acid) has been reported. To date however, PPF-based polymers cross-linked with PEG have not been made. Hence, it remains desirable to provide a poly(propylene fumarate) cross linked with poly(ethylene glycol) and a method for making it. The method for making would preferably include a method for controlling the mechanical properties of the resulting polymer.

SUMMARY OF THE INVENTION

The present invention comprises new, injectable biodegradable polymer composites based on PPF cross linked with biocompatible PEG-DMA and, if desired, β-TCP. The invention further provides the ability to control the crosslinking characteristics of the polymerizing composites and the mechanical properties of cross linked composites by varying the β-TCP content and the double bond ratio of PEG-DMA/PPF. The PPF/PEG-DMA networks produced according to the present invention have clinically acceptable gel times, cross-linking temperature increases of less than 2° C., and are suitable for use as injectable, biodegradable carriers for cell transplantation or drug delivery.

As used herein, the term "network" refers to polymeric molecules that have been cross linked so as to effectively form a continuous molecule. The term "gel" is sometimes used to refer to the same type of cross linked systems.

BRIEF DESCRIPTION OF THE DRAWINGS

For a better understanding of the present invention, reference will be made to the attached Figures, wherein.

DETAILED DESCRIPTION OF A PREFERRED EMBODIMENT

The present invention includes novel PPF-based polymers and a method for making those polymers. The novel polymers comprise PPF cross linked with PEG, in which the fraction of PEG can be varied to control, among other things, the crosslinking characteristics of the composites, including the maximum crosslinking temperature and the gel point, and the properties of the cross linked composites, including its compressive strength and modulus and its water holding capacity.

Synthesis of PPF

PPF is preferably prepared by the method generally described in co-pending application Ser. No. PCT/US99/07912, filed Apr. 9, 1999, and entitled "Synthesis of Poly (Proplyene Fumarate) by Acylation of Propylene Glycol in the Presence of a Proton Scavenger," which is incorporated herein by reference. Briefly, fumaryl chloride is added to a solution of propylene glycol in methylene chloride at 0° C. under nitrogen in the presence of $K_2CO_3$. After addition of fumaryl chloride, the reaction mixture is stirred for an additional 2 hours at 0° C. and then water is added to dissolve the inorganic salt. The organic phase is separated and dried over $Na_2SO_4$. After filtration of the mixture and evaporation of the solvent, the resulting di(2-hydroxylpropyl) fumarate is converted to PPF by transesterification at 160° C. and 0.5 mm Hg.

The resulting polymer can be purified by solution precipitation, forming a viscous liquid. Gel permeation chromatography with a differential refractometer can be used to determine polymer molecular weight distributions.

Crosslinking of PPF

Figure 1:
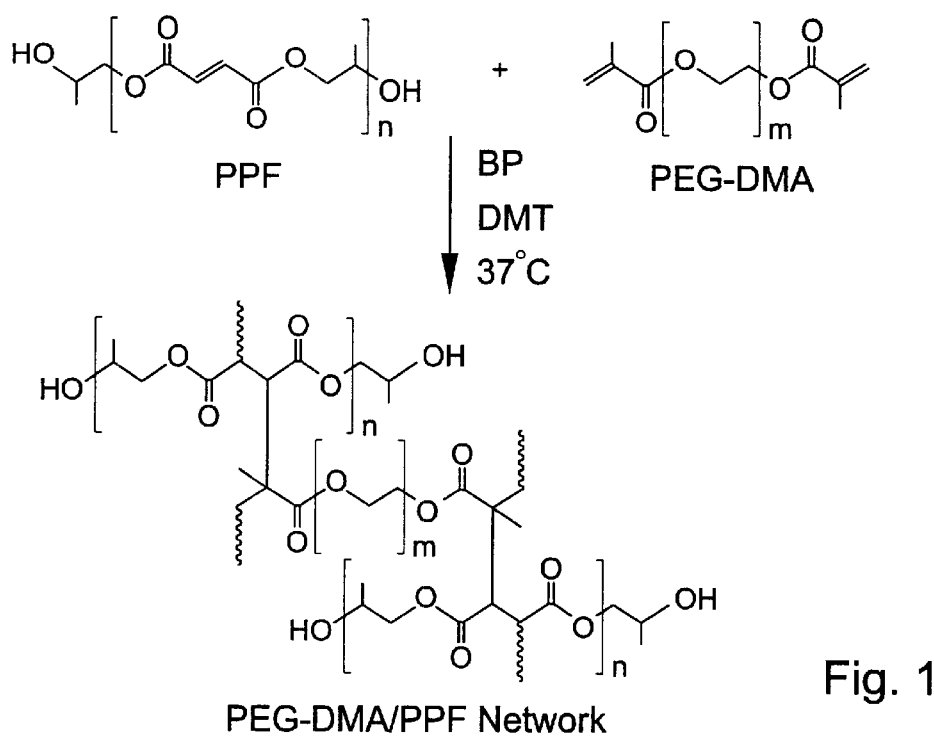
FIG. 1 is a schematic chemical diagram illustrating a possible reaction scheme for crosslinking of PPF with PEG-DMA.

According to the present invention, PPF is crosslinked with PEG-DMA. FIG. 1 shows a possible reaction scheme for this reaction. In preferred reaction, PPF is mixed with PEG-DMA. An amount of BP is dissolved in $CH_2Cl_2$ and the solution is added to the PEG-DMA/PPF mixture. If desired, β-TCP is added, followed by the addition of DMT under rapid stirring for 10 s. Once polymerization starts to take place, a cross linked polymeric network is formed in 10 to 15 min. The light brown polymeric network can be washed with acetone and then water to remove possible unreacted monomers.

EXPERIMENTAL

Materials

Fumaryl chloride (Aldrich, Milwaukee, Wis.) was purified by distillation under nitrogen atmosphere. Propylene glycol, poly(ethylene-glycol)-dimethacrylate (PEG-DMA) (of number average molecular weight 875, liquid), benzoyl peroxide (BP), anhydrous potassium carbonate, Beta-tricalcium phosphate (β-TCP) particles (100 mesh), N,N-dimethyl-p-toluidine (DMT), and all solvents were purchased from commercial sources and used as received.

Experimental Design

Eight composite formulations were examined to assess the effects of PEG-DMA/PPF double bond ratio and β-TCP content on the maximum crosslinking temperature and gel point of the polymerizing composite pastes and also the compressive strength at yield, compressive modulus and equilibrium water content of the crosslinked composites. The different compositions of the composite formulations are set out in Table 1. The double bond ratio of PEG-DMA/PPF was used instead of the weight ratio because PEG-DMA is a macromer. It was calculated as follows: PEG-DMA/PPF double bond ratio=PEG-DMA/PPF weight ratio×(PPF number average molecular weight/PEG-DMA number average molecular weight)×(2/n), where n is the average number of fumarate double bonds in a PPF chain calculated as: n=(PPF number average molecular weight−76)/156.

TABLE 1

BP and DMT contents are 0.3 wt % and 0.15 wt %, respectively, for all formulations.
(Percentage of BP, DMT and β-TCP based on total amount of PEG-DMA and PPF.)

| Formulation | Weight ratio of PEG-DMA/PPF | Double bond ratio of PEG-DMA/PPF | β-TCP content (wt %) |
|---|---|---|---|
| 1 | 1 | 0.38 | 0 |
| 2 | 2 | 0.75 | 0 |
| 3 | 3 | 1.13 | 0 |
| 4 | 5 | 1.88 | 0 |
| 5 | 1 | 0.38 | 33 |
| 6 | 2 | 0.75 | 33 |
| 7 | 3 | 1.13 | 33 |
| 8 | 5 | 1.88 | 33 |

Fumaryl chloride was added dropwise to a solution of propylene glycol in methylene chloride at 0° C. under nitrogen in the presence of $K_2CO_3$. After addition of fumaryl chloride, the reaction mixture was stirred for an additional 2 h at 0° C. and then water was added to dissolve the inorganic salt. The organic phase was separated and dried over $Na_2SO_4$. After filtration of the mixture and evaporation of the solvent, the formed di(2-hydroxylpropyl) fumarate was converted to PPF by transesterification at 160° C. and 0.5 mm Hg. The produced polymer was purified by solution precipitation forming a viscous liquid.

Gel permeation chromatography with a differential refractometer (Waters 410, Milford, Mass.) was used to determine polymer molecular weight distributions. A Phenogel column (300×7.8 mm, 5 nm, mixed bed, Phenomenex, Torrance, Calif.) and a Phenogel guard column (50×7.8 mm, 5 nm, mixed bed, Phenomenex) were employed for a chloroform eluent flow rate of 1 ml/min. Polystyrene standards were utilized to obtain a calibration curve for calculating the polymer molecular weights.

In a typical reaction, 2 g PPF were mixed with 2 g PEG-DMA as a crosslinking reagent. 12 mg BP were dissolved in 0.1 ml $CH_2Cl_2$ and the solution was added to the PEG-DMA/PPF mixture. β-TCP was added for those composites incorporating β-TCP, followed by the addition of 6 μl DMT under rapid stirring for 10 s.

Maximum Temperature

The temperature profile was recorded throughout the crosslinking process in a glass vial of 10 mm diameter and 24 mm length immersed into a 37° C. static water bath. The crosslinking mixture was placed in the glass vial and a thermocouple was inserted to half the depth of the vial. The temperature was measured every minute until it dropped to 37° C. and the maximum temperature was recorded.

Gel Point

The gel point corresponding to the onset of the formation of a polymer network was measured using known viscometry methods. The crosslinking mixture was placed in a Teflon mold of 10 mm diameter and 15 mm height attached to the temperature controlled plate of a rheometer. The addition of DMT to the crosslinking mixture defined time zero. A cylindrical, stainless steel parallel plate geometry of 8 mm diameter was lowered until it was immersed approximately 1 mm into the polymer solution. An oscillatory program consisting of a time sweep at an oscillatory frequency of 1 Hz and magnitude of 0.5% strain was used to monitor the viscosity as the composite cured. The gel point was recorded as the time when the polymer viscosity suddenly increased.

Mechanical Properties

The mechanical properties of PEG-DMA/PPF composites with β-TCP and PEG-DMA/PPF networks were determined under compression. For specimen preparation, the crosslinking mixture was placed into cylindrical vials of 6 mm diameter. After 6 h, the cross linked composites were removed from the vials and cut to 12 mm length cylinders using a diamond saw. The specimens were tested using an 858 Material Testing System mechanical testing machine, following the guidelines set in ASTM F451-95. Samples were compressed at a crosshead speed of 1 mm/min until failure with the load versus deformation curve recorded throughout. The compressive modulus was calculated as the slope of the initial linear portion of the stress-strain curve. The compressive strength at yield was defined by drawing a line parallel to the slope defining the modulus, beginning at 1.0% strain. The intersection of this line with the stress-strain curve was recorded as the compressive strength at yield. For the mechanical testing of wet specimens, the 12 mm length and 6 mm diameter cylinders were placed in phosphate buffered saline (PBS, pH 7.4) for 24 h. Specimens were swollen to approximately 14 mm length and 7 mm diameter, and were tested immediately upon removal from PBS as described above for dry specimens.

Equilibrium Water Content

The equilibrium water content of PEG-DMA/PPF composites with β-TCP and PEG-DMA/PPF networks was determined by gravimetry with cylindrical specimens of 6 mm diameter and 12 mm height. The specimens were washed with 10 ml $CH_2Cl_2$ to remove any unreacted components, air-dried for one day, and vacuum-dried for 6 h. The weight of the dried specimens was then recorded ($W_1$). Subsequently, specimens were immersed in PBS at room temperature. The weight of the specimens was monitored periodically and recorded when it reached an equilibrium value ($W_2$), which occurred after approximately after 24 h. The equilibrium water content was calculated as $[(W_2-W_1)/W_2] \times 100\%$.

Statistical Analysis

All experiments were conducted in triplicate except, for the mechanical testing where n=5. The data were expressed as means±standard deviation. Single factor analysis of variance (ANOVA) was used to assess statistical significance of results.

Results

PPF with number average molecular weight of 1500 (corresponding to an average of 9.1 fumarate double bonds per macromolecular chain) and polydispersity index of 1.87 was obtained after 6 h transesterification. The proton NMR data were: $^1$H-NMR (250 MHz, $CDCl_3$): δ 1.28 (m, $CH_3$), (m, $CH_2$), 5.27 (m, CH), 6.84 (bs, CH=). The integration ratio of the vinyl protons to methyl protons was 2 to 3.4.

The temperature increase during polymerization is an important consideration for injectable, in situ polymerizable formulations. The maximum crosslinking temperature was not affected (p>0.05) by the double bond ratio of PEG-DMA/PPF or the β-TCP content, as shown in Table 2 below. The maximum temperature increase for in vivo cross linking for the eight tested formulations was 1.5° C. and an average of 39.7° C. was calculated for the tested formulations. This relatively small temperature increase makes the present formulations very suitable for in situ polymerization and is much lower than the 94° C. reported for a conventional poly(methyl methacrylate) (PMMA) bone cement tested under similar conditions. The present results also agree with those for injectable hydrogels of poly(propylene fumarate-co-ethylene glycol). The minimal temperature increase also makes the present formulations ideal for use as carriers for cells and/or bioactive molecules or drugs. This is because a excessive temperature increase can cause death or loss of drug bioactivity.

TABLE 2

Maximum crosslinking temperature and gel point for eight composite formulations. Data are presented as means ± standard deviation for n = 3.

| Formulation | Maximum Temperature (° C.) | Gel point (min) |
|---|---|---|
| 1 | 39.4 ± 0.8 | 12.6 ± 2.5 |
| 2 | 39.8 ± 1.0 | 12.0 ± 2.0 |
| 3 | 39.6 ± 0.8 | 10.3 ± 1.8 |
| 4 | 40.0 ± 1.1 | 8.1 ± 0.6 |
| 5 | 39.5 ± 0.6 | 12.3 ± 2.2 |
| 6 | 39.9 ± 1.2 | 11.8 ± 2.0 |
| 7 | 39.4 ± 0.9 | 9.7 ± 1.5 |
| 8 | 40.0 ± 1.5 | 8.0 ± 1.0 |

The gel point data measured under an oscillatory program are also shown in Table 2. The double bond ratio of PEG-DMA/PPF and the β-TCP content did not have an effect (p>0.05) on the gel point, which varied from 8.0±1.0 to 12.3±2.2 min, which is within the range of 5–15 minutes desirable for clinical use, and was not affected by the β-TCP content (P>0.05). In addition, the decrease of gel point with increasing PEG-DMA/PPF double bond ratio was not significant (p>0.05). An increase of the PEG-DMA/PPF double bond ratio should increase the number of active double bonds of methacrylate which may reduce the time frame for crosslinking but also decrease the relative concentration of fumarate double bonds.

Figure 2:
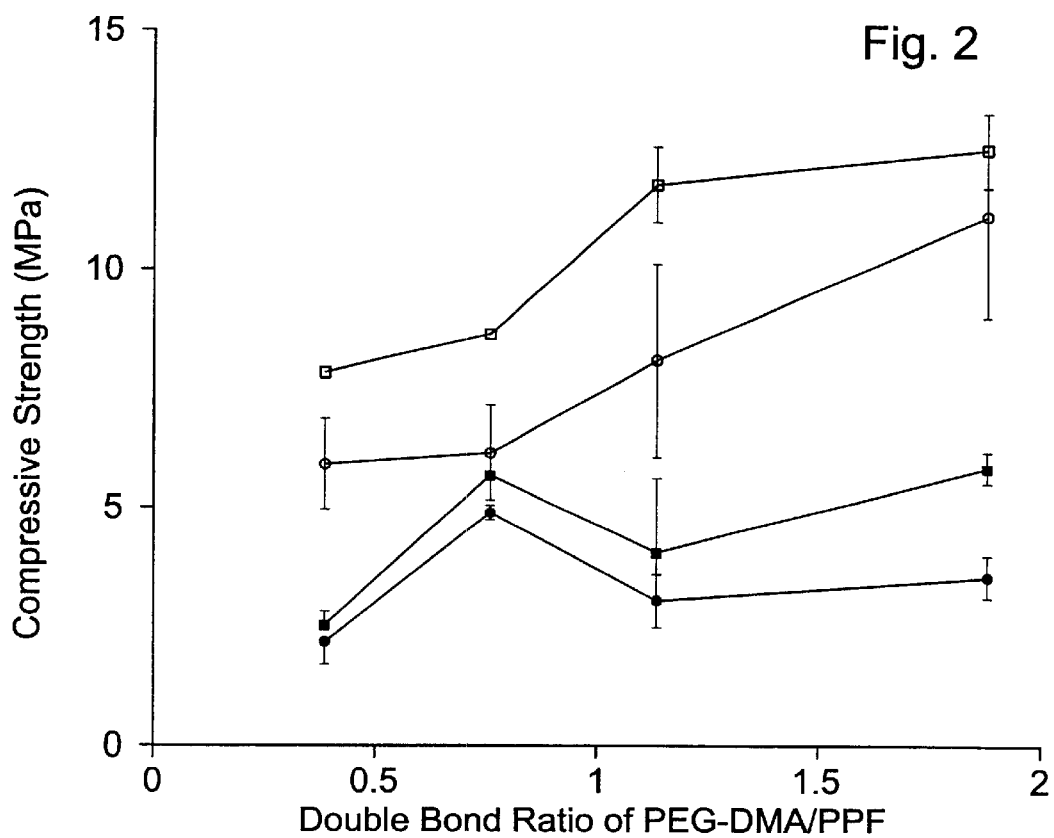
FIG. 2 is a plot illustrating the dependence of compressive strength at yield of PEG-DMA/PPF composites on the double bond ratio of PEG-DMA/PPF for composites incorporating β-TCP (33 wt %) and cross linked polymers without β-TCP, both dry and wet.
Figure 3:
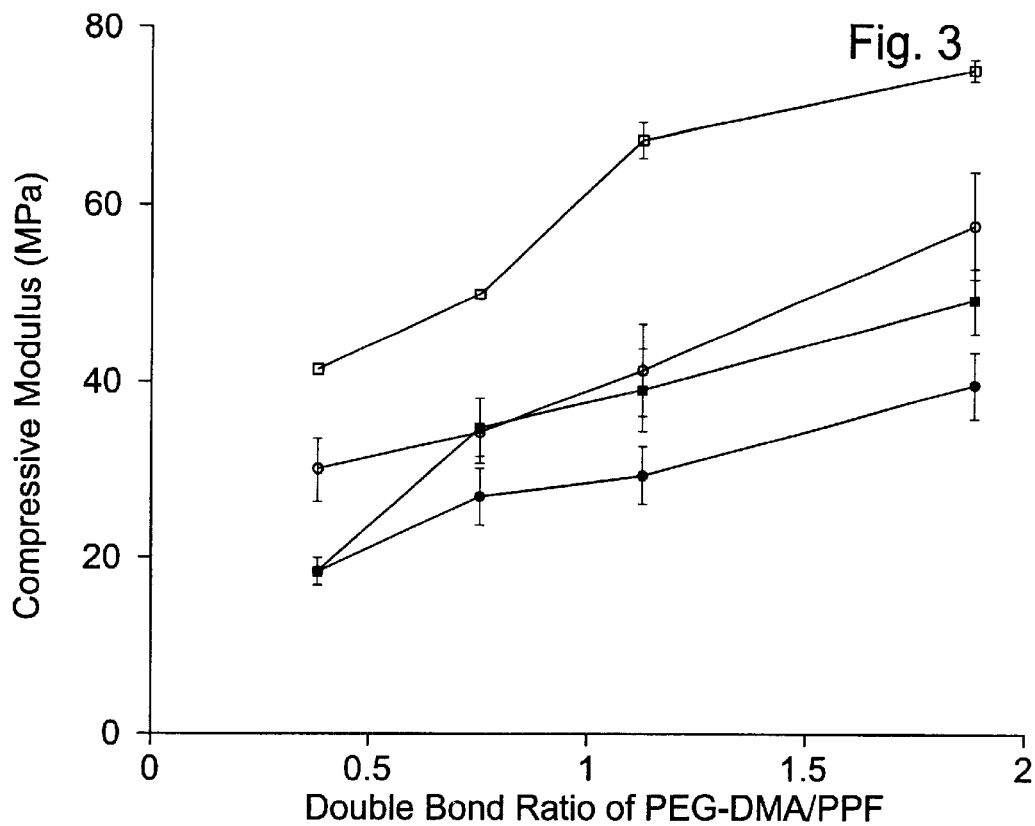
FIG. 3 is a plot illustrating the dependence of compressive modulus of PEG-DMA/PPF composites on the double bond ratio of PEG-DMA/PPF for composites incorporating β-TCP (33 wt %) and crosslinked polymers without β-TCP both tested dry and wet.

An increase in the PEG-DMA/PPF double bond ratio resulted in an increase in both compressive strength at yield and compressive modulus of the networks and cross linked composites, regardless of whether they were tested dry or wet (p<0.05), as shown in FIGS. 2 and 3. FIGS. 2 and 3 show, respectively, the dependence of the compressive strength at yield and the compressive modulus of PEG-DMA/PPF composites on the double bond ratio of PEG-DMA/PPF for composites incorporating β-TCP (33 wt %) (■, ■) and crosslinked polymers without β-TCP (○, ●). Both were tested dry (○, □) and wet (●, ■). Error bars represent means±standard deviation for n=5.

The incorporation of β-TCP caused a further enhancement of the mechanical properties (p<0.05). The compressive strength at yield of the networks tested dry ranged from 5.9±1.0 to 11.2±2.2 MPa, whereas that of the cross linked composites incorporating β-TCP ranged from 7.8±0.1 to 12.6±0.8 MPa. The compressive modulus was in the range of 30.2±3.5 to 58.4±6.2 MPa and 41.4±1.0 to 76.0±1.3 MPa for specimens without β-TCP and incorporating β-TCP, respectively. The compressive strength at yield and compressive modulus of the networks and composites with β-TCP tested wet were lower than the corresponding values of specimens tested dry. For example, in the wet state, the compressive strength at yield of specimens without β-TCP was in the range of 2.2±0.5 to 3.5±0.5 MPa. PEG is a hydrophilic polyether and its incorporation into a PPF network forms a hydrogel with decreased mechanical properties. The reinforcement of the mechanical properties of PEG-DMA/PPF crosslinked composites by β-TCP was not significant for specimens tested wet.

Figure 4:
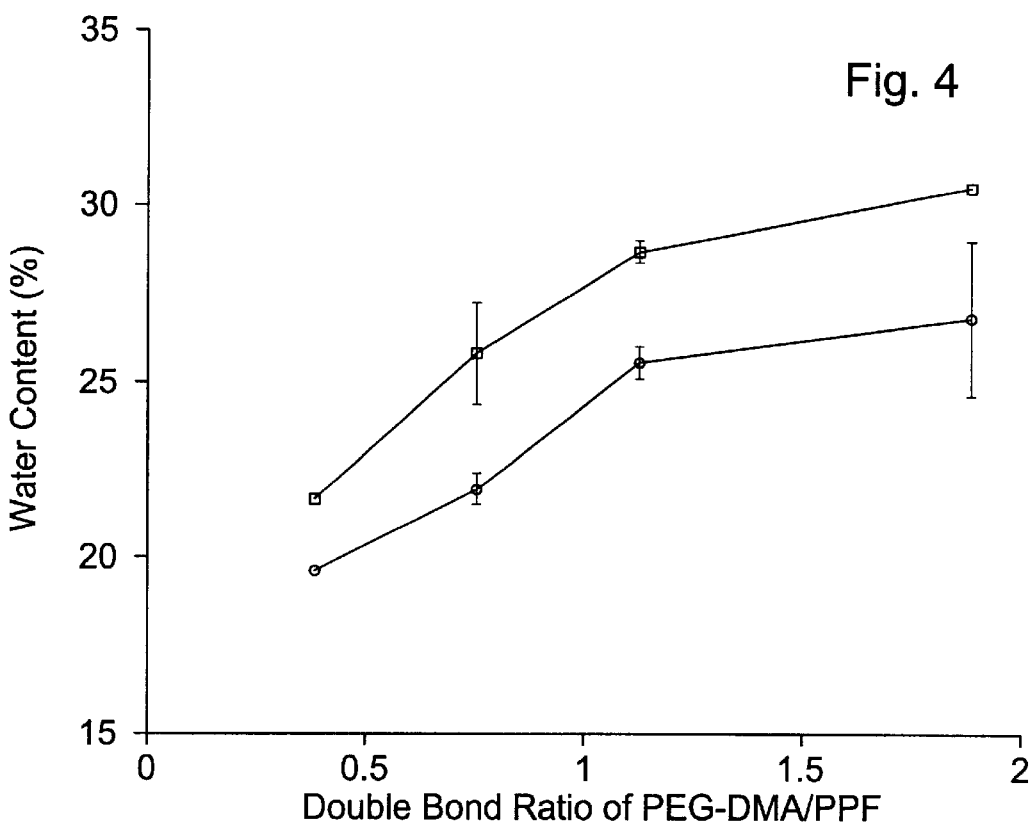
FIG. 4 is a plot illustrating the water content of PEG-DMA/PPF composites incorporating β-TCP and cross linked polymers without β-TCP as a function of the double bond ratio of PEG-DMA/PPF after equilibrium in PBS.

The equilibrium water content of PEG-DMA/PPF networks increased from 21.7±0.2 to 30.7±0.2% as the PEG-DMA/PPF double bond ratio increased from 0.38 to 1.88, as shown in FIG. 4. FIG. 4 shows the water content of PEG-DMA/PPF composites incorporating β-TCP (■) and crosslinked polymers without β-TCP (○) as a function of the double bond ratio of PEG-DMA/PPF after equilibrium in PBS. Error bars represent means±standard deviation for n=3. Incorporation of β-TCP into the cross linked composites reduced their water content ($p<0.05$).

The present method for making PPF avoids the addition of a catalyst, which might otherwise be brought into the cross linked composite with PPF as an impurity. Moreover, the absence of a catalyst minimizes the reaction of the fumarate double bonds during PPF synthesis. The proton NMR spectrum of PPF indicated that the integration ratio of the vinyl protons to the methyl protons was 2:3.4, which was close to the ratio of 2:3.33 calculated from the number average molecular weight, thus suggesting no loss of PPF unsaturation.

The crosslinking density of PEG-DMA/PPF networks increased with the PEG-DMA/PPF double bond ratio resulting in increased mechanical properties of the PEG-DMA/PPF networks and crosslinked composites. The mechanical properties of the PEG-DMA/PPF networks did not suggest a PEG-DMA self-polymerization. This phenomenon can occur in PPF networks crosslinked with N-vinyl pyrrolidone due to formation of long cross links. No apparent volume changes were observed upon crosslinking.

Hence, it is possible to cross link PPF with PEG-DMA to form biodegradable hydrogels with tailored mechanical properties by varying the PEG-DMA/PPF double bond ratio. Although the mechanical properties of porous hydrogels may prove insufficient for replacement of human trabecular bone, the use of injectable, in situ crosslinkable hydrogels holds promise for the engineering of softer orthopaedic tissues such as cartilage.

What is claimed is:

1. A polymer network comprising poly(propylene fumarate) and poly(ethylene glycol)-dimethacrylate formed from an injectable, in situ crosslinkable composite formulation, said composite formulation comprising poly(propylene fumarate) and poly(ethylene glycol)-dimethacrylate wherein said poly(propylene fumarate) and poly(ethylene glycol)-dimethacrylate are each present in an amount effective to produce a polymeric network useful for in vivo applications when said composite formulation is crosslinked.

2. An injectable, in situ crosslinkable, polymerizable, biodegradable composite formulation comprising poly(propylene furarate) and poly(ethylene glycol)-dimethacrylate, wherein said poly(propylene fumarate) and poly(ethylene glycol)-dimethacrylate are each present in an amount effective to produce a polymeric network useful for in vivo applications when said composite formulation is crosslinked.

3. The composition according to claim 2, further including beta-tricalcium phosphate.

4. The composition according to claim 2 wherein the composition exhibits a temperature increase of less than 2° C. during cross linking.

5. The composition according to claim 2 wherein the composition exhibits a gel point between 5–15 minutes.

6. The composition according to claim 2 wherein the injectable, in situ crosslinkable, polymerizable, biodegradable composite formulation comprises a carrier for cell transplantation.

7. The composition according to claim 2 wherein the injectable, in situ crosslinkable, polymerizable, biodegradable composite formulation comprises a carrier for bioactive drug delivery.

8. A polymer network formed from a crosslinkable polymerizable biodegradable composite formulation, said composite formulation comprising poly(propylene fumarate) and poly(ethylene glycol)-dimethacrylate, wherein said poly(propylene fumarate) and said poly(ethylene glycol)-dimethacrylate are each present in a proportion that provides said network with desired physical properties.

9. An injectable, in situ crosslinkable, polymerizable, biodegradable composite formulation, comprising poly(propylene fumarate) and poly(ethylene glycol)-dimethacrylate, wherein said poly(propylene fumarate) and said poly(ethylene glycol)-dimethacrylate are each present in a proportion that provides said biodegradable composite formulation with desired physical properties.

10. An injectable, in situ crosslinkable, polymerizable, biodegradable composite formulation comprising poly(propylene fumarate) and poly(ethylene glycol)-dimethacrylate, wherein the double bond ratio of PEG-DMA/PPF is between about 0.38 and about 1.88.

11. The composition according to claim 10 wherein the polymer network comprises a biodegradable carrier for cell transplantation.

12. The composition according to claim 10 wherein the polymer network comprises a biodegradable carrier for bioactive drug delivery.

* * * * *